United States Patent [19]
Berg et al.

[11] Patent Number: 5,304,700
[45] Date of Patent: Apr. 19, 1994

[54] SEPARATION OF METHYLENE CHLORIDE FROM N-PENTANE BY EXTRACTIVE DISTILLATION

[75] Inventors: Lloyd Berg, 1314 South Third Ave., Bozeman, Mont. 59715; Zuyin Yang, Bozeman, Mont.

[73] Assignee: Lloyd Berg, Bozeman, Mont.

[21] Appl. No.: 94,698

[22] Filed: Jul. 22, 1993

[51] Int. Cl.$^5$ .......................... C07C 7/00; C01B 31/00
[52] U.S. Cl. ........................... 585/864; 585/866; 423/414
[58] Field of Search ................ 585/864, 866; 423/414

[56] References Cited
U.S. PATENT DOCUMENTS 4,345,976  8/1982  Peter et al. ........................... 208/348

Primary Examiner—Anthony Mc Farlane
Assistant Examiner—Nhat A. Phan

[57] ABSTRACT

Methylene chloride cannot be completely separated from n-pentane by conventional distillation or rectification because of the minimum boiling azeotrope. Methylene chloride can be readily separated from n-pentane by extractive distillation. Typical effective agents are 2-pentanone, isopropyl acetate or methanol.

2 Claims, No Drawings

SEPARATION OF METHYLENE CHLORIDE FROM N-PENTANE BY EXTRACTIVE DISTILLATION

FIELD OF THE INVENTION

This invention relates to a method for separating methylene choride from n-pentane using certain organic compounds as the agent in extractive distillation.

DESCRIPTION OF PRIOR ART

Extractive distillation is the method of separating close boiling compounds or azeotropes by carrying out the distillation in a multi-plate rectification column in the presence of an an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. When the compounds to be separated normally form an azeotrope, the proper agents will cause them to boil separately during the extractive distillation and this make possible a separation in a rectification column that cannot be done at all when no agent is present. The extractive agent should boil higher than any of the close boiling liquids being separated and not form minimum azeotropes with them. Usually the extractive agent is introduced a few plates from the top of the column to insure that none of the extractive agent is carried over with the lowest boiling component. This usually requires that the extractive agent boil twenty Celcius degrees or more higher than the lowest boiling component.

At the bottom of a continuous column, the less volatile components of the close boiling mixtures and the extractive agent are continuously removed from the column. The usual methods of separation of these two components are the use of another rectification column, cooling and phase separation or solvent extraction.

Methylene chloride, B. P.=40° C. forms a minimum boiling azeotrope with n-pentane, B. P.=36.1° C. at 35° C. containing 49% methylene chloride. The methylene chloride - n-pentane azeotrope is impossible to separate by distillation because the relative volatility of an azeotrope is 1.0. Extractive distillation would be an attractive method of effecting the separation of methylene chloride from n-pentane if agents can be found that (1) will enhance the relative volatility between methylene chloride and n-pentane and (2) are easy to recover, that is, form no azeotrope with methylene chloride or n-pentane and boil sufficiently above these compounds to make separation by rectification possible with only a few theoretical plates.

Extractive distillation typically requires the addition of an equal amount to twice as much extractive agent as the methylene chloride-n-pentane on each plate of the rectification column. The extractive agent should be heated to about the same temperature as the plate into which it is introduced. Thus extractive distillation imposes an additional heat requirement on the column as well as somewhat larger plates. However this is less than the increase occasioned by the additional agents required if the separation is done by azeotropic distillation. Another consideration in the selection of the extractive distillation agent is its recovery from the bottoms product. The usual method is by rectification in another column. In order to keep the cost of this operation to a minimum, an appreciable boiling point difference between the compound being separated and the extractive agent is desirable. It is desirable that the extractive agent be miscible with methylene chloride otherwise it will form a two-phase azeotrope with the methylene chloride in the recovery column and some other method of separation will have to be employed.

TABLE 1

| Effect of Relative Volatility on the Separation of n-Pentane From Methylene Chloride at 99% Purity by Extractive Distillation | | | |
|---|---|---|---|
| Relative Volatility | Theoretical Plates | Actual Plates 75% Efficiency | Actual Plates 75% Eff., Min Reflux |
| 1.2 | 50 | 67 | 87 |
| 1.3 | 35 | 47 | 61 |
| 1.4 | 27 | 36 | 47 |
| 1.5 | 23 | 31 | 40 |
| 1.6 | 20 | 27 | 35 |
| 1.7 | 17 | 23 | 29 |

The advantage of employing an effective extractive distillation agent for this separation is shown in Table 1. Ordinary rectification cannot completely separate n-pentane from methylene chloride because of the minimum azeotrope. When extractive distillation is employed with an agent that converts the relative volatility to 1.5, only 31 actual plates are required.

OBJECTIVE OF THE INVENTION

The objects of this invention are to provide a process or method of extractive distillation that will enhance the relative volatility of n-pentane to methylene chloride in their separation in a rectification column. It is a further object of this invention to identify organic compounds that are stable, can be separated from methylene chloride by rectification with relatively few plates and can be recycled to the extractive distillation column with little decomposition.

SUMMARY OF THE INVENTION

The objects of this invention are provided by a process for the separation of n-pentane from methylene chloride which entails the use of certain organic compounds as the agent in extractive distillation.

DETAILED DESCRIPTION OF THE INVENTION

We have discovered that certain organic compounds will effectively increase the relative volatility between n-pentane and methylene chloride and permit the separation of n-pentane from methylene chloride by rectification when employed as the agent in extractive distillation. Table 2 lists the agents that we have found to be effective. The data in Table 2 was obtained in a vapor-liquid equilibrium still. In every case, the starting mixture was the n-pentane-methylene chloride azeotrope. The relative volatilities are listed for each of the agents investigated. The compounds which are effective are ethyl acetate, n-propyl acetate, isopropyl acetate, n-butyl acetate, isobutyl acetate, n-amyl acetate, isoamyl acetate, methyl acetate, vinyl acetate, methyl vinyl acetate, methyl ethyl ketone, 3-pentanone, methyl isobutyl ketone, 2-pentanone, dioxane, 4-methyl-2-pentanone, 3-methyl-2-butanone, 2,4-pentanedione, methyl propionate, 2,2-dimethoxypropane, ethyl propionate, ethyl butyrate, vinyl butyl ether, pyridine, ethyl valerate, propyl butyrate, 1-methoxy-2-propanol, isopropanol, methanol and ethanol.

Isopropyl acetate whose relative volatility had been determined in the vapor-liquid equilibrium still was then evaluated in a glass perforated plate rectification column possessing 7.3 theoretical plates and the results listed in Table 3. After two hours of continuous operation, a relative volatility of 1.95 was obtained with this extractive agent.

THE USEFULNESS OF THE INVENTION

The usefulness or utility of this invention can be demonstrated by referring the data presented in Table 2 and 3. All of the successful agents show that n-pentane can be separated from methylene chloride by extractive distillation in a rectification column and that the ease of separation as measured by relative volatility is considerable.

WORKING EXAMPLES

Example 1

Eighty grams of the n-pentane-methylene chloride azeotrope and 30 grams of isopropyl acetate were charged to a vapor-liquid equilibrium still and refluxed for five hours. Analysis indicated a vapor composition of 48.5% n-pentane, 51.5% methylene chloride; a liquid composition of 29.5% n-pentane, 70.5% methylene chloride which is a relative volatility of n-pentane to methylene chloride of 2.2.

TABLE 2

Effective Agents For Separating
n-Pentane From Methylene Chloride

| Compounds | Relative Volatility |
| --- | --- |
| Ethyl acetate | 1.8 |
| n-Propyl acetate | 2.2 |
| Isopropyl acetate | 2.0 |
| n-Butyl acetate | 2.5 |
| Isobutyl acetate | 1.35 |
| n-Amyl acetate | 2.3 |
| Isoamyl acetate | 2.9 |
| Methyl acetate | 1.6 |
| Vinyl acetate | 1.75 |
| Methyl vinyl acetate | 3.2 |
| Methyl ethyl ketone | 2.8 |
| 3-Pentanone | 3.2 |
| Methyl isobutyl ketone | 2.9 |
| 2-Pentanone | 4.0 |
| 4-Methyl-2-pentanone | 2.8 |
| 3-Methyl-2-butanone | 3.5 |
| 2,4-Pentanedione | 2.5 |
| Dioxane | 3.3 |
| Methyl propionate | 4.4 |
| 2,2-Dimethoxypropane | 1.5 |
| Ethyl propionate | 1.7 |
| Ethyl butyrate | 1.5 |
| Vinyl butyl ether | 1.6 |
| Pyridine | 3.3 |
| Ethyl valerate | 1.8 |
| Propyl butyrate | 1.45 |
| 1-Methoxy-2-propanol | 2.1 |
| Isopropanol | 1.35 |
| Methanol | 3.5* |
| Ethanol | 3.3* |

*Brings out Methylene chloride as overhead

TABLE 3

| | Data From Run Made In Rectification Column | | | |
| --- | --- | --- | --- | --- |
| Agent | Column | Time hrs. | Weight % n-Pentane | Weight % CH$_2$Cl$_2$ | Relative Volatility |
| Isopropyl acetate | Overhead | 1 | 95 | 5 | 1.50 |
| | Bottoms | | 50.6 | 49.4 | |
| Isopropyl acetate | Overhead | 2 | 82 | 18 | 1.95 |
| | Bottoms | | 3.3 | 96.7 | |

Example 2

Seventy grams of the n-pentane-methylene chloride azeotrope and 30 grams of methanol were charged to the vapor-liquid equilibrium still and refluxed for four hours. Analysis indicated a vapor composition of 43.4% methylene chloride, 56.6% n-pentane; a liquid composition of 18% methylene chloride, 82% n-pentane which is a relative volatility of methylene chloride to n-pentane of 3.5.

Example 3

A solution comprising 110 grams of n-pentane and 90 grams of methylene chloride was placed in the stillpot of a 7.3 theoretical plate rectification column. When refluxing began, an extractive agent comprising isopropyl acetate was pumped into the column at a rate of 15 ml/min. The temperature of the extractive agents as it entered the column was 65° C. After establishing the feed rate of the extractive agent, the heat input to the n-pentane-methylene chloride in the stillpot was adjusted to give a total reflux rate of 40 ml/min. After two hours of operation at total reflux, the overhead and bottoms samples of approximately two ml. were collected and analysed. The overhead analysis was 82% n-pentane, 18% methylene chloride and the bottoms analysis was 3.3% n-pentane, 96.7% methylene chloride. This gives an average relative volatility of 1.95 for each theoretical plate. This data is presented in Table 3.

We claim:

1. A method for recovering n-pentane from a mixture of n-pentane and methylene chloride in the presence of about one part by weight of an extractive agent per part of n-pentane-methylene chloride mixture, recovering n-pentane as overhead product and obtaining the methylene chloride and the extractive agent as bottoms product, wherein said extractive agent consists of one material selected from the group consisting of methyl acetate, ethyl acetate, n-propyl acetate, isopropyl acetate, n-butyl acetate, isobutyl acetate, n-amyl acetate, isoamyl acetate, vinyl acetate, methyl vinyl acetate, methyl ethyl ketone, 3-pentanone, methyl isobutyl ketone, 2-pentanone, dioxane, 4-methyl-2-pentanone, 3-methyl-2-butanone, 2,4-pentanedione, methyl propionate, 2,2-dimethoxypropane, ethyl propionate, ethyl butyrate, vinyl butyl ether, pyridine, ethyl valerate, propyl butyrate, 1-methoxy-2-propanol and isopropanol.

2. A method for recovering methylene chloride from a mixture of methylene chloride and n-pentane which comprises distilling said mixture of methylene chloride and n-pentane in the presence of about one part by weight of an extractive agent per part methylene chloride-n-pentane mixture, recovering methylene chloride as overhead product and obtaining the n-pentane and the extractive agent as bottoms product, wherein said extractive agent consists of methanol or ethanol.

* * * * *